(12) United States Patent
Neev

(10) Patent No.: US 8,282,630 B2
(45) Date of Patent: *Oct. 9, 2012

(54) HOME USE DEVICE AND METHOD FOR TREATING SKIN CONDITIONS

(76) Inventor: Joseph Neev, Laguna Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,694

(22) Filed: Jun. 19, 2011

(65) Prior Publication Data

US 2012/0010606 A1    Jan. 12, 2012

Related U.S. Application Data

(63) Continuation of application No. 11/752,893, filed on May 23, 2007, now Pat. No. 7,981,112, which is a continuation-in-part of application No. 10/150,632, filed on May 17, 2002, now abandoned, which is a continuation-in-part of application No. 09/694,738, filed on Oct. 23, 2000, now abandoned, which is a continuation of application No. 09/132,537, filed on Aug. 11, 1998, now Pat. No. 6,168,590, said application No. 11/752,893 is a continuation-in-part of application No. 11/234,771, filed on Sep. 23, 2005.

(60) Provisional application No. 60/921,901, filed on Apr. 4, 2007, provisional application No. 60/802,960, filed on May 23, 2006, provisional application No. 60/704,602, filed on Aug. 1, 2005, provisional application No. 60/678,968, filed on May 9, 2005, provisional application No. 60/615,510, filed on Oct. 2, 2004, provisional application No. 60/055,577, filed on Aug. 12, 1997.

(51) Int. Cl.
*A61B 18/04* (2006.01)

(52) U.S. Cl. .......... 606/27; 606/28; 606/32; 607/98
(58) Field of Classification Search .......... None
See application file for complete search history.

(56) References Cited

U.S. PATENT DOCUMENTS

| | | | | |
|---|---|---|---|---|
| 6,280,438 B1 * | 8/2001 | Eckhouse et al. | ............... | 606/9 |
| 6,402,739 B1 * | 6/2002 | Neev | ............... | 606/9 |
| 6,408,212 B1 * | 6/2002 | Neev | ............... | 607/100 |
| 6,482,199 B1 * | 11/2002 | Neev | ............... | 606/10 |
| 6,508,785 B1 * | 1/2003 | Eppstein | ............... | 604/113 |
| 6,685,699 B1 * | 2/2004 | Eppstein et al. | ............... | 606/2 |
| 6,717,102 B2 * | 4/2004 | Neev et al. | ............... | 219/121.68 |
| 6,922,578 B2 * | 7/2005 | Eppstein et al. | ............... | 600/347 |
| 7,020,528 B2 * | 3/2006 | Neev | ............... | 607/100 |
| 7,163,536 B2 * | 1/2007 | Godara | ............... | 606/34 |
| 7,244,253 B2 * | 7/2007 | Neev | ............... | 606/9 |
| 7,494,492 B2 * | 2/2009 | Da Silva et al. | ............... | 606/99 |
| 2004/0005349 A1 * | 1/2004 | Neev | ............... | 424/443 |
| 2005/0055055 A1 * | 3/2005 | Neev | ............... | 607/3 |
| 2006/0074468 A1 * | 4/2006 | Neev | ............... | 607/90 |
| 2006/0129214 A1 * | 6/2006 | Da Silva et al. | ............... | 607/109 |
| 2006/0142750 A1 * | 6/2006 | Da Silva et al. | ............... | 606/27 |
| 2007/0255359 A1 * | 11/2007 | Neev | ............... | 607/90 |

* cited by examiner

*Primary Examiner* — Henry M Johnson, III
*Assistant Examiner* — Lynsey Crandall
(74) *Attorney, Agent, or Firm* — J. Peter Paredes; Rosenbaum & Silvert, P.C.

(57) ABSTRACT

Skin tissue is subjected to thermal energy that creates heating of the area being treated causing pores and follicle ducts to open so that excess oil, sebum, fatty deposits, or other unwanted deposits can be removed. A vacuum device is used to direct suction to the treated skin area helping to remove the unwanted deposits. Patterned thermal modification of tissue is used to expedite healing and minimize pain. The heating is controlled so that no skin tissue is damaged while still providing enough heat to the skin to alter the flow of sebum and destroy bacteria in the treated area.

21 Claims, 10 Drawing Sheets

HOME USE DEVICE AND METHOD FOR TREATING SKIN CONDITIONS

RELATED APPLICATIONS

This application is a continuation of U.S. application Ser. No. 11/752,893 filed May 23, 2007, now U.S. Pat. No. 7,981, 112; and which also is a continuation-in-part of U.S. application Ser. No. 11/234,771 filed Sep. 23, 2005 which claims priority to provisional patent application 60/615,510 filed Oct. 2, 2004, provisional application No. 60/704,602 filed Aug. 1, 2005, and provisional application 60/678,968 filed May 9, 2005; and which also further claims priority to provisional application No. 60/802,960 filed May 23, 2006, and provisional application No. 60/921,901 filed Apr. 4, 2007; all of which are incorporated herein in their entirety by reference.

FIELD OF THE INVENTION

The present invention relates generally to the application of energy to biological tissue, and specifically to the application of electromagnetic energy to the skin in order to treat various skin diseases.

BACKGROUND

It is known in the art to apply electromagnetic energy to biological tissue to engender changes therein. Sunbathers, for example, regularly expose themselves to bright sunlight in order to increase melanocyte activity in the basal layer of the epidermis, responsive to the sun's ultraviolet (UV) radiation. Artificial UV sources have been created to satisfy the desire for a healthy-looking tan in the winter. Other forms of electromagnetic energy, laser-light in particular, are currently used in a large range of therapeutic and cosmetic procedures, including eye surgery, hair removal, wrinkle removal, and tattoo removal.

PCT publication WO 98/55035, which is incorporated herein by reference, describes methods for minimizing injury to biological tissue surrounding a site exposed to pulses of electromagnetic energy. This and all other extraneous materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

U.S. Pat. No. 5,720,894 to Neev et al., which is incorporated herein by reference, describes biological tissue processing using Ultrashort Pulse High Repetition Rate Laser System for Biological Tissue Processing.

It is known in the art to use UV and blue light to cure acne. A beam of short wavelength light is irradiated and is supposed to destroy bacteria through sterilizing ability of the high energy photon to disrupt molecular bond and photochemical destruction of living cells. This method is deficient however, because of the relatively short depth of penetration of the short wavelengths regime and the danger of mutagenetic effect as well as the effective shielding of deeper lying bacteria by superficial skin structures.

It is also known in the art to use chemical peels and tretinoin to chemically peel of the outer layer of the skin. This method is deficient however, because of side effect, long response time and longer time duration between application of the treatment and results and various side effects.

It is also known in the art to apply antibiotic to patients in order to combat active acne. This method is deficient however, since the application of antibiotic is non-selective, often done systemically and thus affects the entire body, and also for the fact that various organisms and bacteria develop resistance to antibiotics and thereby increases the risk of exposure to bacteria that are now resistant to antibiotics.

It is also known in the art to combat active acne by treating and controlling hormonal activity within a patient body. Again, this is a systemic approach that suffers from many side effects including, in some cases, severe depression, and impact on the entire body.

It is therefore desirable to have a simple, non-invasive, non-systemic treatment method and apparatus for the treatment and cure of acne, that, when applied, is free of side effects, yet is safe and effective. It is also desirable to have a method that is easy to apply and is relatively quick and easy to administer and produces rapid skin response, relief of symptoms, and cure for the condition.

It is also desirable to have a simple, safe, non-invasive, non-systemic treatment method and apparatus for the treatment and cure of other skin diseases and skin conditions, that, when applied, is free of side effects, yet is safe and effective. Finally, it is particularly desirable to have a safe, home use, small and compact device that consumers can carry with them or use in the home or office environment for treatment of pimples, acne, or minor skin conditions, with or without the application and use of medicine or topical medication, to resolve irritating skin conditions, including acne.

SUMMARY OF THE INVENTION

The present invention provides methods and apparatus in which a region of intact living skin is treated with energy pulses having a duration of short duration, at an average energy density such that a temperature at the surface rises to at least 45° C. without substantially denaturing tissue at the epidermal/dermal junction. The basic principle is to heat up the surface of the skin with sufficient heat to cause opening of the pores, but limit the amount of energy such that when it is diffused and distributed over a larger volume (in the dermis), the energy is below that which would cause substantial denaturation of cells in the skin.

In especially preferred embodiments the energy pulses are produced by an electric heater coupled to a capacitor and a battery, the capacitor discharges between 0.2 $J/cm^2$ to 10 $J/cm^2$ and preferably between 0.5 $J/cm^2$ and 5 $J/cm^2$ and most preferably between 0.7 $J/cm^2$ and 3 $J/cm^2$ in pulses of between 0.1 ms and 10 ms. The energy pulses are preferably electromagnetic radiation that includes visible wavelengths.

To avoid overheating of, and damage to, the dermis and underlying tissues, the pulses have durations of less than 30 seconds, more preferably less than 10 seconds, and in some cases less than 1 second, less than 0.1 sec, or even less than 0.01 sec. Pulses can be repeated at any desirable frequency, including especially between 0.5 second and 10 seconds, and more preferably between about 2 second and 5 seconds. Unless a different meaning is dictated by the context, all ranges herein should be interpreted as being inclusive of their endpoints. Interpulse delays of between 0.2 sec and 10 sec are preferred, with interpulse delays of between 2 sec and 5 sec even more preferred. Thus, it is contemplated that the controller could cooperate with the energy source to subject the treatment region to at least 2 energy pulses within a 20 second period, and possibly at least 10, 25, 50, 75 or even a 100 such energy pulses within a 20 second period.

In other aspects of preferred embodiments, the tip treatment area is preferably between 0.2 mm and 10 cm in diameter, and preferably between about 2 mm and about 2 cm in diameter.

From a method standpoint, it is contemplated to operate a device as described herein such that hair follicles in the skin expand without being permanently damaged. By appropriately selecting pulse energy density, pulse width, and interpulse delays, it is possible to raise the surface temperature of the skin at least 60° C. or even 70° C. or more without substantially denaturing tissue at the epidermal/dermal junction. In some cases this effect can be facilitated by actively cooling the surface of the skin to a temperature of less than 50° C.

It is still further contemplated that operation of devices as described herein can include treating the skin with anti-microbial radiation that includes blue to ultraviolet wavelengths (to achieve an antimicrobial effect), and applying a vacuum to the skin within 5, 10, or 15 minutes of application of the pulse (to help remove debris released during the heating portion of the treatment).

In a preferred embodiment of the present invention, the tissue of the skin is subjected to localized heating for a given time and in a defined location, which elevates the temperature of the skin in that location as compared to its normal temperature. This elevation of skin temperature corresponds to expansion and displacement of a portion of the skin, thus leading to the opening of skin pores.

In another preferred embodiment of the present invention, the tissue of the skin is subjected to localized heating for a given time and in a defined location, which elevates the temperature of the skin in that location as compared to an adjacent location. This elevation of skin temperature corresponds to expansion and displacement of a portion of the skin with respect to the adjacent location, thus leading to the opening of skin pores.

In a further preferred embodiment, an intermediate substance which is capable of absorbing at least a portion of the electromagnetic energy from a source, is placed between the energy source and the skin. The intermediate substance absorbs the source energy and converts it to heat. Being in contact with the skin, the intermediate substance elevates the temperature of the skin to cause to an expansion and displacement, leading to the opening of skin pores and relieving of acne conditions.

In yet a further preferred embodiment, an intermediate substance which is capable of absorbing at least a portion of the electromagnetic energy from a source, is placed between the energy source and the skin. The intermediate substance absorbs the source energy and converts it to heat. Being in contact with the skin, the intermediate substance elevates the temperature of the skin in one location as compared to an adjacent location. This elevation of skin temperature corresponds to expansion and displacement of a portion of the skin with respect to the adjacent location, thus leading to the opening of skin pores.

As will be apparent from the description contained herein, aspects of the inventive subject matter include:

a. Providing an improved apparatus and methods for applying energy to a material;
b. Providing an improved apparatus and methods for removing heat generated during application of electromagnetic energy to a material;
c. Providing an improved apparatus and methods for removing heat generated during application of electromagnetic energy to biological tissue;
d. Providing an improved apparatus and methods for decreasing pain during application of electromagnetic energy to biological tissue;
e. Providing an improved apparatus and methods for performing medical treatments;
f. Providing an improved apparatus and methods for performing cosmetic treatments;
g. Providing an improved apparatus and methods for healing of skin diseases and skin illnesses;
h. Providing an improved apparatus and methods for enabling an electromagnetic energy source to allow healing of skin diseases and skin illnesses or to improve conditions;
i. Providing methods and apparatus for enabling a chemical, RF, Microwave, mechanical, electric, magnetic, or ultrasound energy source to advance healing skin diseases and skin illnesses;
j. Providing improved methods and apparatus for enabling a low-power electromagnetic energy source to advance healing of skin diseases and skin illnesses substantially without pain, while substantially minimizing the amount of damage or modification to remaining tissue;
k. Providing improved methods and apparatus for enabling a low-power electromagnetic energy source to perform skin treatment, treatment of acne and treatment that prevent the occurrence of acne; and
l. Providing improved methods and apparatus for enabling a low-power electromagnetic energy source to perform tissue treatment that cures acne and relieves symptoms of acne.

These and other objects, features, aspects and advantages of the inventive subject matter will become more apparent from the following detailed description of preferred embodiments, along with the accompanying drawings in which like numerals represent like components.

DETAILED DESCRIPTION

Figure 1A:
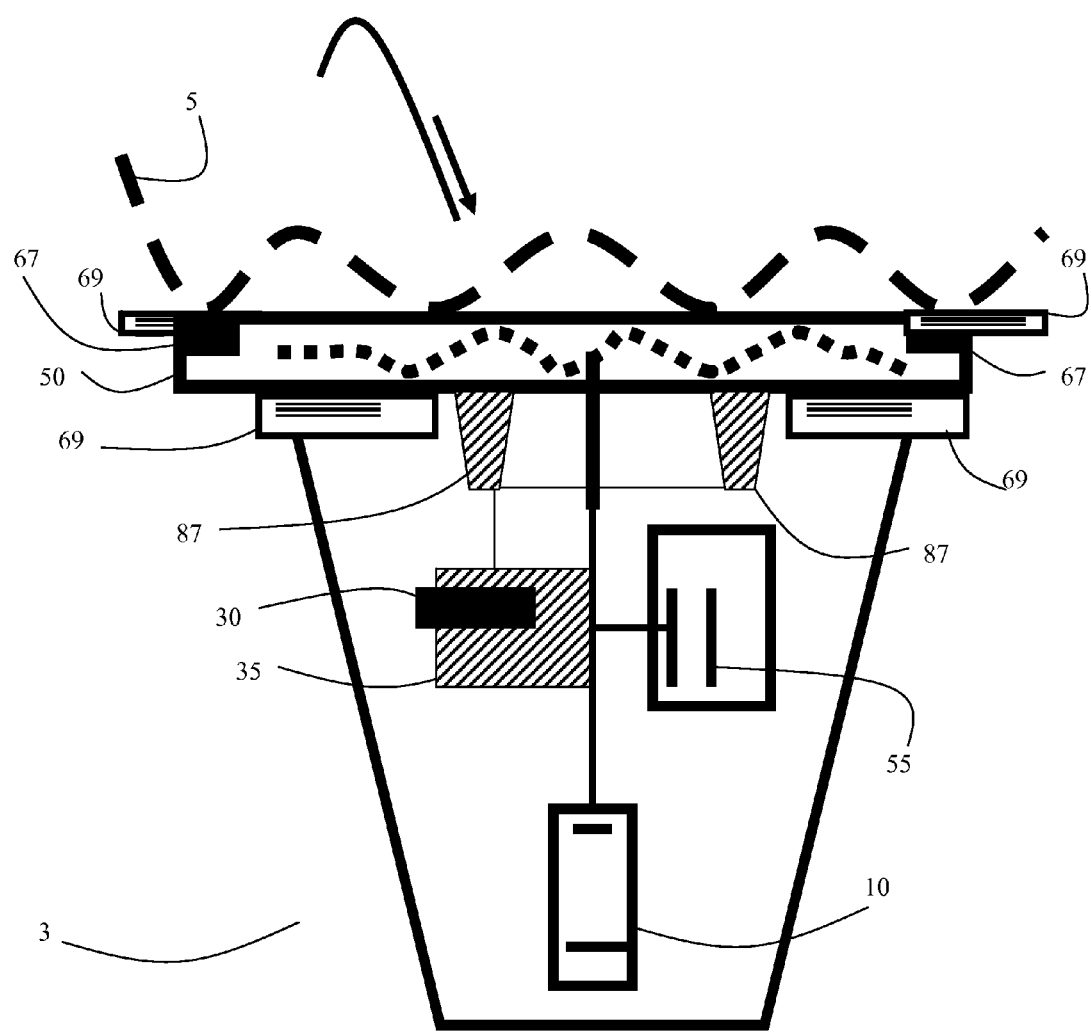
FIG. 1A is a simplified diagram of an apparatus for treatment of acne and skin condition and its components.

Devices and methods are contemplated herein for treatment of a variety of skin conditions, and in particular, cyst, acne, aged skin, and wrinkles. In FIG. 1A the device 3, designed to treat a skin surface 5, comprises the following components: an energy source 10, for example, a battery, an electro-mechanical dynamo, or an electric wall outlet, among other possible energy sources, that provide energy to the device control elements 30, for example a control element on a circuit board 35. The device control elements 30 are activated by input switches (not shown), for example, a power level switch, a trigger switch, or an off/on switch, that allows the user to interface with the device, for example they allow the user to control the operation, power level and activation of the device. The device control elements 30 allows the energy source 10 to power a treatment head 50 directly or to charge up a plurality of capacitors 55 or other intermediate elements (resistors, diodes, etc.) that modify the energy output of the treatment heads. The treatment head 50 can include a resistor that provides heating to the skin by diffusion.

Figure 1B:
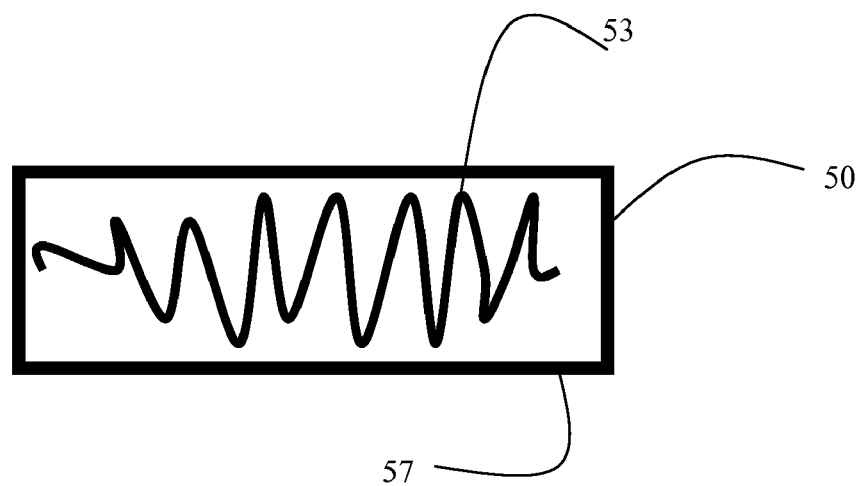
FIGS. 1B and 1C are simplified diagrams of contemplated heating elements.
Figure 1C:
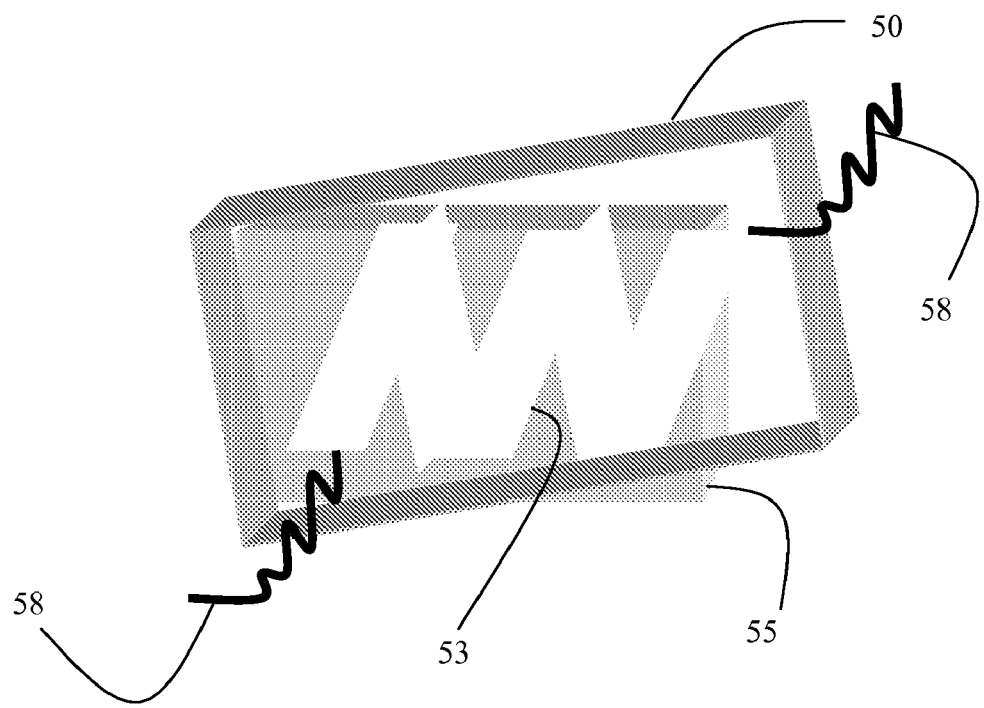

In preferred embodiments of FIGS. 1B and 1C, the treatment head 50 can be made from a heating element, for example a resistor 53 can be embedded in an insulating material 57, for example PTFE or a plastic material that is sufficiently thin to allow rapid conduction of the thermal energy to the skin. In another preferred embodiment, the resistor 53 can be made of a conductor in a flat configuration so that it conducts heat uniformly in a planar configuration of temperature gradient as shown in FIG. 1C This will allow the heat to diffuse as a flat planar diffusion of thermal energy to the skin. The resistor 53 can be mounted on a layer of glass or PTFE, plastic, or other insulating material 57, which reduces removal of thermal energy from the resistor, and facilitates diffusion of the thermal energy by conduction towards the targeted skin. Between the resistor 53 and the target skin one can advantageously include a thin layer of electrically insulating material 57 that prevents electricity from the resistor 53 from reaching the skin but allows thermal energy from the resistor 53 to reach the skin. The resistor 53 can be made of typical materials known in the art such as copper, aluminum, tungsten, steel, nichrome, or copper and tin alloys.

Resistor 53 can advantageously be coated with a thin layer of electrically insulating but thermally conducting material that allows the heat to flow but prevents electric current from reaching the skin—for example by anodizing processes. The treatment head 50 can have any suitable thickness, preferably 10 micrometers to 1 mm, more preferably between 25 micrometers and 500 micrometers, and most preferably between 50 micrometers and 200 micrometers. The electrical insulating layer 57 can also have any suitable thickness, preferably between 5 micrometers and 1 mm, more preferably between 10 micrometers and 500 micrometers, and most preferably between 20 micrometers and 250 micrometers.

Because the maximum amount of energy that is loaded up onto the heater element is the maximum amount of energy (or heat) available to treat and also to possibly cause excessive collateral damage, it determines the upper limit of the risk of the method and the device contemplated herein. The upper limit of the amount of energy provided by the resistor 53 is determined by its heat capacity (for example, the most energy a heating element can have is the full amount of energy from a discharging capacitor, $1/2CV^2$, where C is the capacitor capacitance and V is the final voltage across the capacitor). If the heating element is completely insulated, and is designed to reach a temperature increase DT above normal skin temperature (for example, if we designate DT=200°), then the amount of energy that will allow it to reach that temperature is determined by the heat capacity of the heating element 53. The heat capacitance is a function of the heating element volume and hence for a designated treatment area (for example between about 0.2 cm$^2$ to about 9 cm$^2$, and preferably 2 cm$^2$) a thinner heating element will have smaller heat capacitance and hence will store less energy, corresponding to its designated temperature DT. Thus, by proper design of the heat capacitance and thickness of the heater, we can calculate and limit the upper value of energy available for transfer into the skin. For this reason, a thin heater will serve to limit the amount of energy available for heating of the skin. For example, a total thickness of the heating element 53 should be between 20 micrometers and about 500 micrometers, and preferably between about 30 micrometers and about 300 micrometers. As shown in FIG. 1C, the wires 58 provide current to the resistive heating element 53.

A temperature monitoring element 67 (for example, a thermo couple or an IR detector, such as an HgCdTe detector) can be integrated into the heating element as shown in FIG. 1A, and be operatively coupled to the heating element 53. A cooling element 69, for example a thermoelectric cooler(or TEC), can also be integrated into the treatment head 50 to reduce the temperature of the treatment head 50 before the next shot is fired. For example, a reduction in temperature range between about 25° C. to 45° C., and preferably between about 27° C. and about 37° C, can be required before the device can be fired again.

Figure 1D:
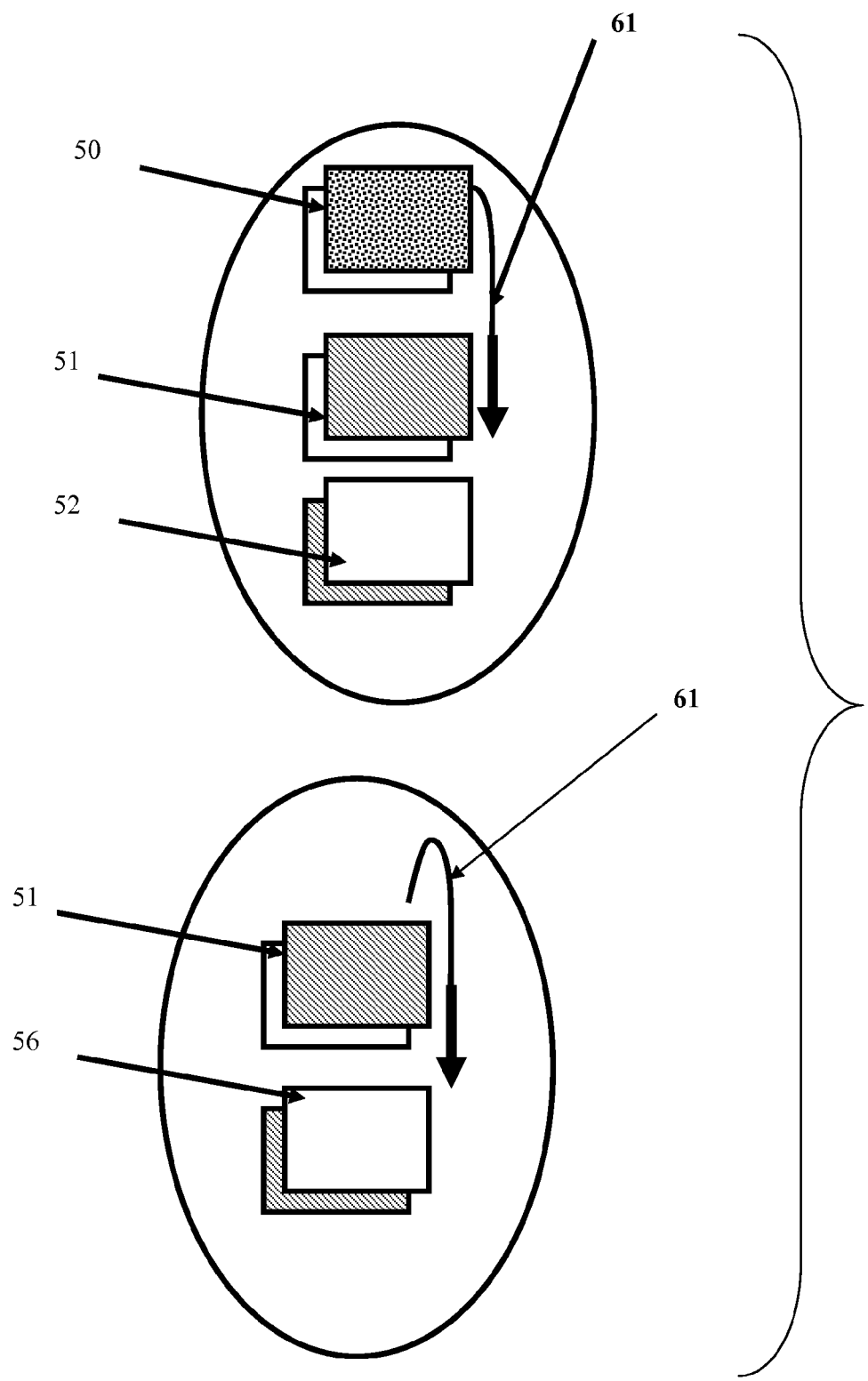
FIG. 1D is a simplified diagram of an array of heating elements.

As shown in FIG. 1D, a plurality of treatment heads can be used. Thus, heads 51, 52 can be used while treatment head 50 is cooling. For convenience, the treatment heads 50, 51 and 52 can all be mounted on a conveyer belt or other actuator, and thereby moved in the direction of the arrow 61.

Figure 1E:
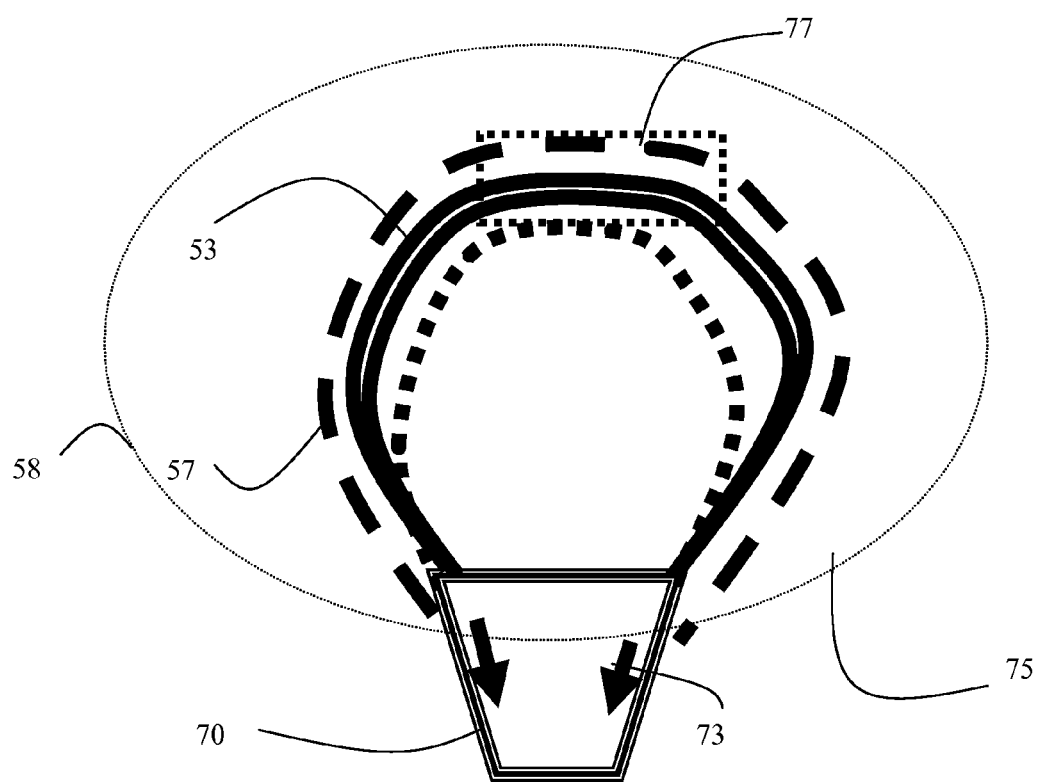
FIG. 1E is a simplified diagram of an alternative treatment head.

In FIG. 1E an alternative treatment head 75 includes heating element 53 mounted on insulating material 57 and flexible layer 59. Treatment head 75 is flexible, and is mounted on a collapsible/extendable rack 70, which can be extended or expanded in the direction of the arrows 73, pulling with it the entire assembly of treatment head 75, in respect to a variable treatment area 77. The variable size treatment area 77 can range, for example, from about 0.5 mm in diameter to about 5 cm in diameter, and preferably from about 2 mm in diameter to 25 mm in diameter.

The above treatment head cooling and adjustable head size may not be necessary if a simple handheld device is desired. Thus, in general, a preferred embodiment includes a device for treatment of skin conditions comprising: an energy source adapted and configured to provide energy to the skin surface; and a controller adapted and configured to automatically energize the energy source so it heats the skin to a temperature sufficient to loosen, dislodge destroy or otherwise desirably modify the blockage within a follicle so as to allow drainage thereof in response to a user input.

Heating elements 53 can be coated for several reasons, including to enhance safety, to provide quicker temperature changes, and for improved patient experience. For example, as shown in FIGS. 1B and 1C a resistor 53 can be embedded in an insulating material 57. For example, PTFE or other plastic or glass electrically insulating material that allow the heat to thermally conduct and reach the skin 5 can be used. In some contemplated embodiments a thin electrically insulating coating (for example, a thin plastic coating can be applied or an anodizing process can be used) can be applied to the resistor 53 to prevent electrical current from reaching the skin 5, while still allowing heat to diffuse and reach the skin 5.

It is contemplated that controller 30 can operate to cease providing energy to the heating element 53, and to reheat the heating element 53 without a further user input.

It is also contemplated that energy source provided to the skin can causes substances inserted in the hair follicle to expand.

It is also contemplated that the energy source 10 and controller 50 can be co-located in a housing, and that the housing can be sized and dimensioned to be hand held.

One or more energy removal (i.e., cooling) elements 69 may also be used. The energy removal element 69 should be adapted and configured to cool said heating element 53 and/or a skin surface 5 to a temperature of less than about 50° C., and an electromagnetic source of energy in the blue to ultraviolet range is also applied to achieve sterilization of the skin 5.

Particularly preferred methods and apparatus include: a heating element 53 adapted and configured to contact a skin surface 5; and a controller 30 adapted and configured to automatically heat the heating element 53 to a temperature sufficient to loosen, dislodge, destroy or otherwise desirably modify a blockage within a follicle or improve the condition and health of the skin 5 in response to a user input. Such devices can advantageously raise the temperature surface of the skin 5 to above 38° C., more preferably to above 45° C., and in some cases could transiently raise the temperature of the surface of the skin 5 to 70° C., or even 100° C., 200° C., 250° C., 300° C., 350° C. or more.

Of course, such high temperatures would be maintained for only a short period of time, to avoid substantial permanent damage to the majority of the living cells in the skin. Thus, the contemplated devices and methods would preferably not be applied in an ablative manner. To that end elevated heating of the surface of the skin would typically occur for a heating period that is less than about one second, more preferably less than about 0.1 second more preferably yet less than about 0.01 second and most preferably less then about 1 ms.

Also contemplated herein are methods of treating a subject having a skin lesion, comprising applying energy to a lesion; heating the lesion to a temperature sufficient to modify skin condition and treat disease but cause serious burn; and repeating the energy applications and heating steps at least one time.

Figure 2:
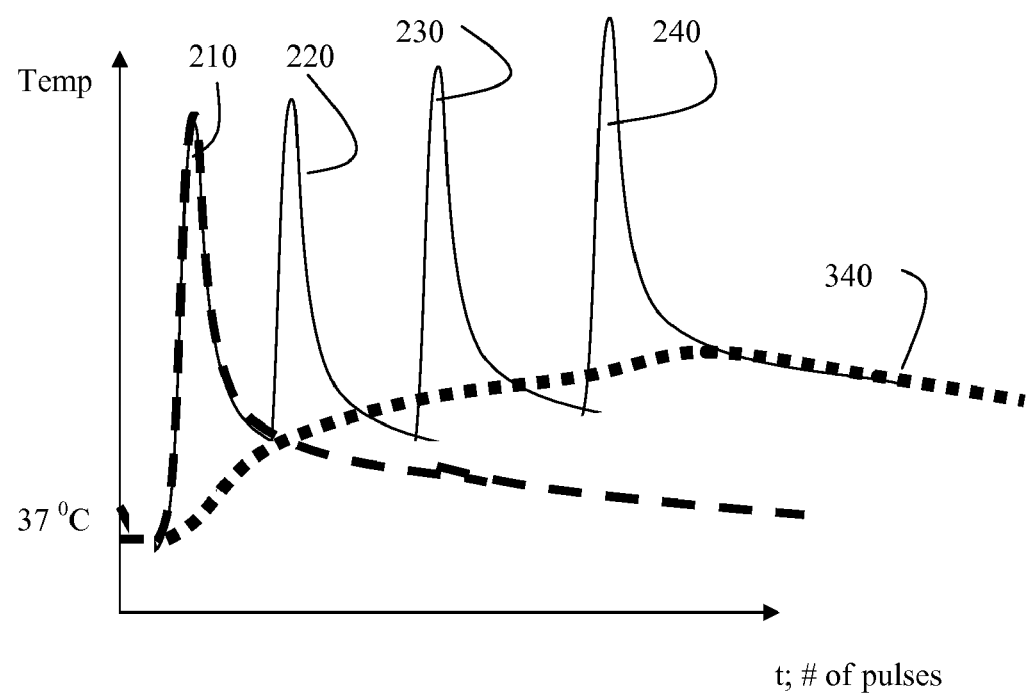
FIG. 2 is a simplified diagram showing a representative heat accumulation and temperature vs. pulse number effect on the skin surface.

For example, if an electric current is used to heat up a resistor, for example by charging up and discharging a capacitor through the resistor as is contemplated by one preferred embodiment, or, for example, by providing a DC or AC current through the resistor adapted to contact the skin, and using automated or manual interruption to terminate the current flow and heating phase, then repeating the heating cycle will result in accumulation of heat in the skin and temperature build up, for example, as shown in FIG. 2.

As shown in FIG. 2, the temperature of the skin due to the first heating cycle 210 is a peak temperature, for example, 300° C., and then decays to lower values due to conduction to the skin 5 and some loss to the insulating material 57 of FIG. 1A. A second pulse, for example a few seconds later, may raise the temperature of the skin 5 which has not yet been able to decay to its normal ambient temperature, for example 37° C., and has only reached a lower temperature of 45° C., will now rise again due to cycle number 2, for example to a peak temperature of 310° C. as shown in 220. A third pulse will raise the peak temperature for example to 320° C. peak and will decay to a temperature of, for example, 50° C. We can see that the accumulation of thermal energy from repeated heating cycles 1, 2, and 3, and 4, as shown by the curves 210, 220, 230 and 240, will result in a slow average skin temperature increase, as shown by the curve 250 from its ambient temperature 37° C. to an elevated temperature 50° C. The tail of the curve 210 (broken line) shows what the decay of a single pulse will look like.

The number of such repeated heating cycles should be limited or spaced apart by several seconds to allow cooling between pulses, or utilize active cooling such as thermoelectric cooling or cryogen spray cooling incorporated with the method or device to prevent accumulation of excess heating of the skin surface, which can lead to deeper tissue effects or burn. The heating step, if done through a slower heating process, should be limited in time or monitored with the thermocouple 67 of FIG. 1A. If limited in time, this preferred heating step should preferably be limited to less than 3 minutes, more preferably to less than 1 minute, more preferably yet to less than 30 second, more preferably yet to less than 1 second, more preferably yet to less than 100 ms, more preferably yet to less than 10 ms, more preferably yet to less than 1 ms, and more preferably yet to less than 0.1 ms.

In an additional preferred embodiment, an electrical device 3 for the treatment of skin lesions comprises: (a) an interface 50 for contacting the skin 5 of a subject; (b) a heater 53 capable of heating the interface to a temperature sufficient to cause expansion of a hair follicle and treatment of skin conditions without irreversible damage to living cells. The device 3 may optionally include an energy removal (i.e., cooling) element 69, preferably capable of cooling the heating element 53 and/or treatment surface to a temperature of less than about 50° C. Still further, the device may include a source of electromagnetic energy 87 in the blue to ultraviolet range, which can be applied to at least partially sterilize the skin 5.

Figure 3:
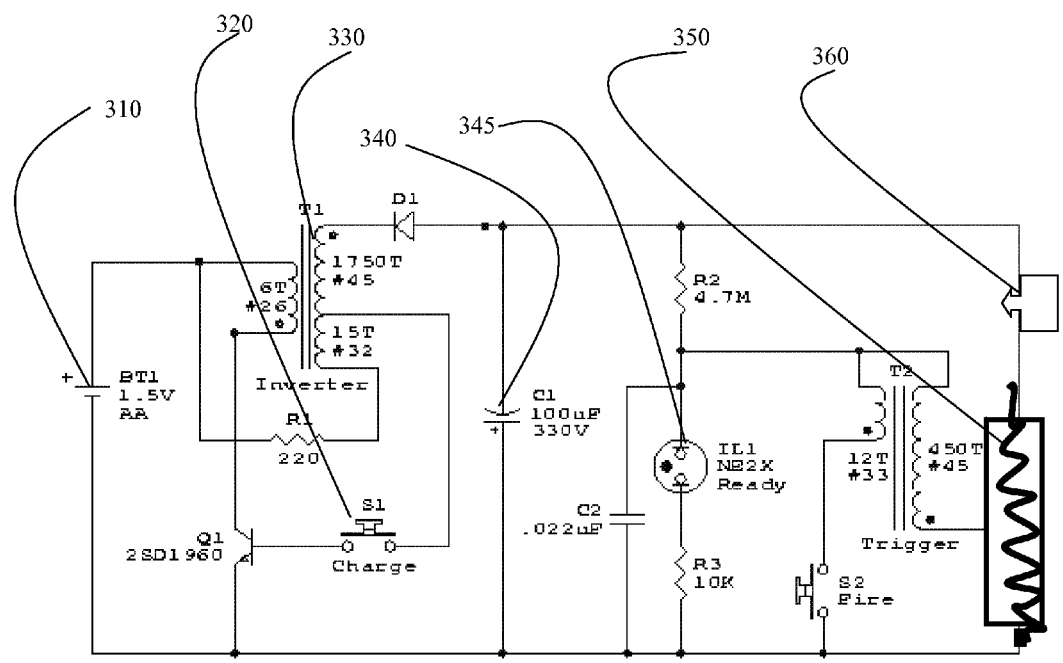
FIG. 3 is a simplified diagram of a possible circuit diagram for an electic heater skin and acne treatment device.

FIG. 3 shows one possible circuit diagram to pulse a flash lamp 350. A switch 320 is turned on to draw power from battery 310, through transformer 330, to activate the device and charge the capacitor 340. When the capacitor is fully charged a lamp 345 (or LED) is turned on and the circuit is ready to fire. Push button 360 is pressed to discharge capacitor 340. After firing, the capacitor 340 begins to charge, and after several seconds (depending on the battery and resistance) is fully charged. This circuit releases a maximum energy per pulse of ½ $CV^2$, where C is the capacitance of capacitor 340 and V is the final voltage across the capacitor 340. By selecting appropriate values of C and V, the released energy can be kept at the appropriate level so it loads up sufficient amount of energy into the top layer of the tissue. For example, a discharge time of 1 ms will allow diffusion into about 30 micrometer of tissue with thermal conductivity similar to that of water, thus the amount of energy in this tissue should be enough to cause a temperature jump high enough to cause sufficient tissue expansion so that pores and spacing in the epidermis are opened to allow healing of acne and other skin conditions. However, the amount of energy discharged and conducted into the tissue is not enough to cause serious collateral damage or serious burn because the total amount of energy per unit volume conducted into the deeper tissue, i.e. less than ½ $CV^2$, is too low to interact with the living cells and cause significant irreversible damage or a serious burn).

Figure 4:
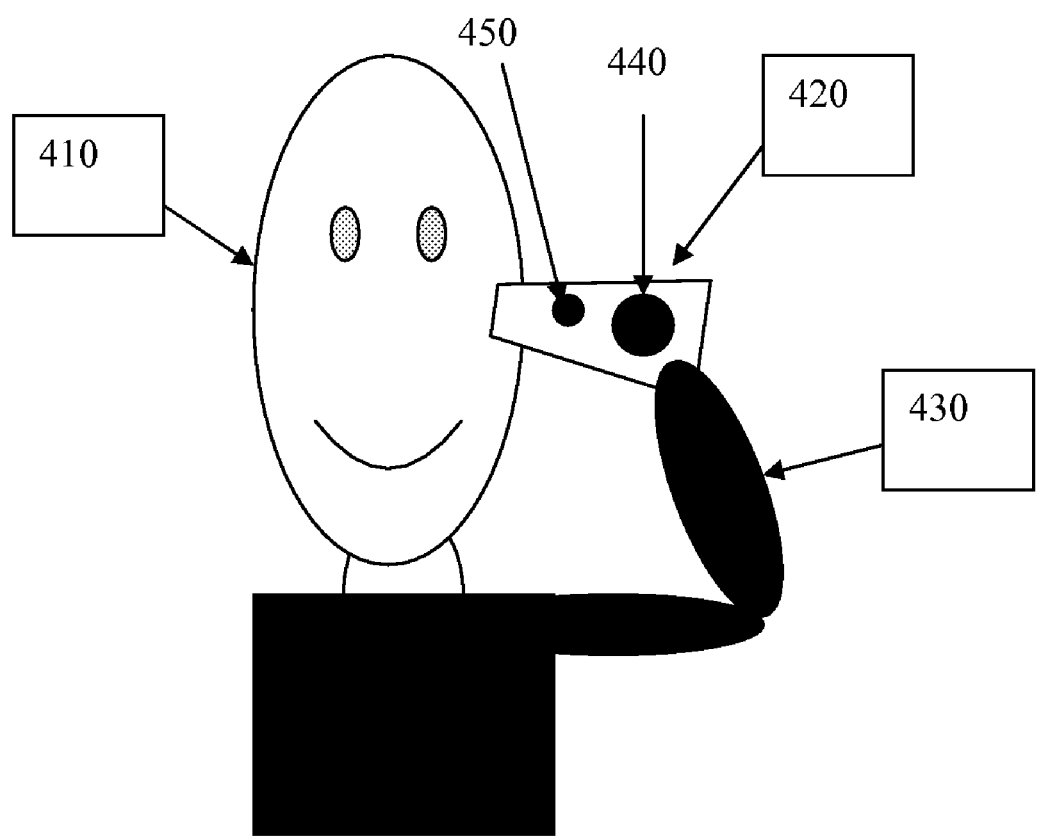
FIG. 4 is a simplified diagram showing how a handheld skin treatment device is used to treat the skin.

FIG. 4 shows how the device 420 can be used by a consumer suffering from acne or other skin conditions. The use 410 holds the device 420 in his hand 430, and push a charge button 440 to initiate charging and a fire button 450 to fire the device 420 once it has made good contact with the user's face.

Figure 5:
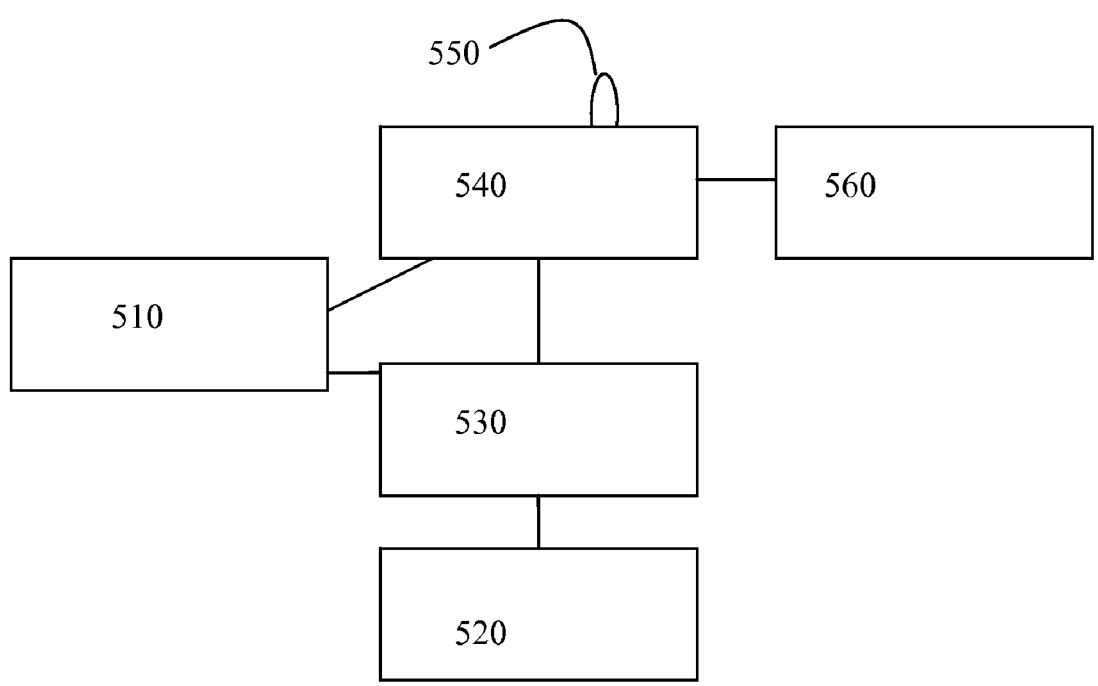
FIG. 5 is a simplified block diagram of device components.

In FIG. 5, 510 is a source of energy, for example, a battery or a wall plug; 520 is a user interface such as a power control, a charge button and a fire button; 530 is a microprocessor powered by the power source 510 and controlling the firing sequence, charging times, firing repletion rate, and power levels, the microprocessor 530 being responsive to a user input; 540 is a capacitor and pulse generator assembly capable of using the power source 510 to charge the capacitor and store the electrical energy; 550 is the full charge indictor telling the user that the device is ready to fire; and 560 is a heater adapted to contact the skin to heat the skin surface to the required level.

An additional preferred embodiment of the present invention contemplates a device for treatment of skin conditions and acne, the device comprising: an energy source adapted and configured to provide energy to the skin surface; a controller adapted and configured to automatically energize the energy source so it heats the skin to treat said skin conditions and acne; and a vacuum source to be applied to the skin before, during or after the energy application to said skin. In a preferred embodiment, an energy source is applied to the skin. The energy may be, for example, a laser, a broad lamp, a flash lamp, an RF energy source, and ultrasound beam, or a microwave energy source.

Figure 6:
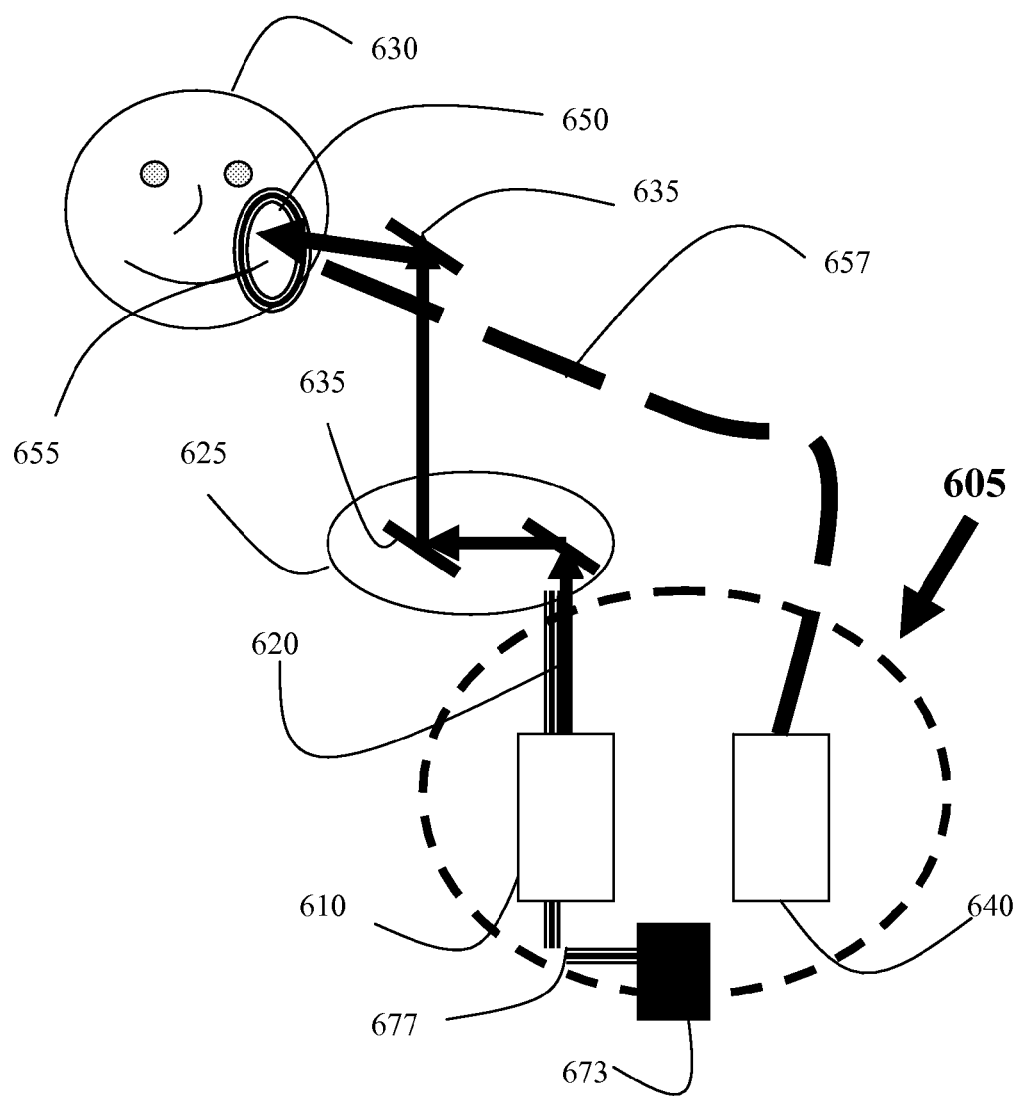
FIG. 6 is a simplified diagram of an acne and skin treatment device utilizing an energy source and a source of suction to enhance treatment.

As shown in FIG. 6, the device 605 comprises an energy source 610 which delivers energy to the surface of the skin 650 of a user 630. A source providing suction, for example a vacuum pump 640, delivers suction to the surface of the skin 650 at the same location that the energy is applied. The suction can be applied to the skin 650 before, during, or after the application of energy to the skin 650. The suction can help clean pores, enhance energy delivery to target tissue and skin components, remove debris, sebum, fat, bacteria, or smoke from the surface, clean pores and hair follicle openings as well as sweat pores, and minimize the sensation of pain. The source of energy 610 can be one of the following: mechanical, thermal, electrical, optical, electromagnetic, ultrasound, microwave, nuclear, chemical, or RF energy. It emits a beam 620 that can be manipulated with lenses, mirrors and scanners 635, as well as other optical components 625, or may be adapted to directly contact the skin 650 of the user 630.

In an additional preferred embodiment, the device 605 may also comprise an intermediate element capable of converting some energy to thermal energy and conducting sufficient thermal energy to the skin to open and clean skin pores and follicle openings, treat skin ailments, and improve skin condition and look. The thermal energy thus generated may also be applied in conjunction with the application of suction before, during, or after the thermal energy or other energy application.

In further preferred embodiments, the device 605 may additionally and preferably comprise an energy removal element, said energy removal element adapted and configured to cool said heating element and/or a skin surface to a temperature of less than about 50° C., and an electromagnetic source of energy in the blue to ultraviolet range is also applied to achieve sterilization of the skin 650. A source of coolant 673, for example a gas container can dispense coolant, for example through a coolant dispensing tube 677. Alternatively, a TEC can be used to cool the target skin. The device 605 can advantageously also incorporate a contact suction head, for example a plurality of suction heads 655 attached with a plurality of tubes 657 to a plurality of vacuum pumps 640 so that the suction is applied to the targeted skin area 650 before during or after the application of energy.

Devices and methods can also advantageously comprise: an energy source adapted and configured to provide energy to the skin surface; and a controller adapted and configured to automatically energize the energy source so it heats the skin to a temperature sufficient to treat skin conditions and wrinkles the device may further comprise an intermediate material, which may contain a substance capable of absorbing said energy, said absorbing substance arranged in patterns that maximize the penetration of light while at the same time creating surface heating on the skin surface. This will allow the deeper penetrating energy to heat from below while the upper surface heating creates heat flow downward from the surface. The partial heating of the surface also allow faster healing as smaller portions of the epidermis are damaged. For example, surface heating of the upper layers of the skin can be between about 0% to about 70% and preferably between 3% and 50%.

The intermediate absorbing material may contain a laser absorbing substance arranged in patterns that maximize the penetration of light to depths of between about 100 micrometers to about 1 mm in order to maximize penetration of the light to heat the sebaceous glands and minimize secretion of sebum. The preferred density for deeper laser light penetration and direct light heating of the upper layers of the skin is between about 0% to about 70% and preferably (if surface heating utilizing the intermediate absorbing material is taken into account) between 3% and 50%. A laser in the blue to ultraviolet range can be used in order to utilize the sterilization effect of these wavelengths, as well as generating heat. The heat generation will be increased due to the increased absorption resulting from the shorter wavelengths. In addition, blue and green to orange wavelengths are more readily absorbed by the hemoglobin in the blood and thus enhance heat generation at the surface of the skin and in layers below the surface.

Various tissue conditions can be effectively treated using a plurality of microscopic treatment zones. In that regard zones can be between 1 micrometer in diameter and 7 mm in diameter, preferably between 20 micrometers and 300 micrometers in diameter, and most preferably between 50 micrometer in diameter and about 250 micrometers in diameter. Zones can advantageously be created in a predetermined treatment pattern, wherein a subset of said plurality of discrete microscopic treatment zones includes individual discrete microscopic treatment zones.

Figure 7:
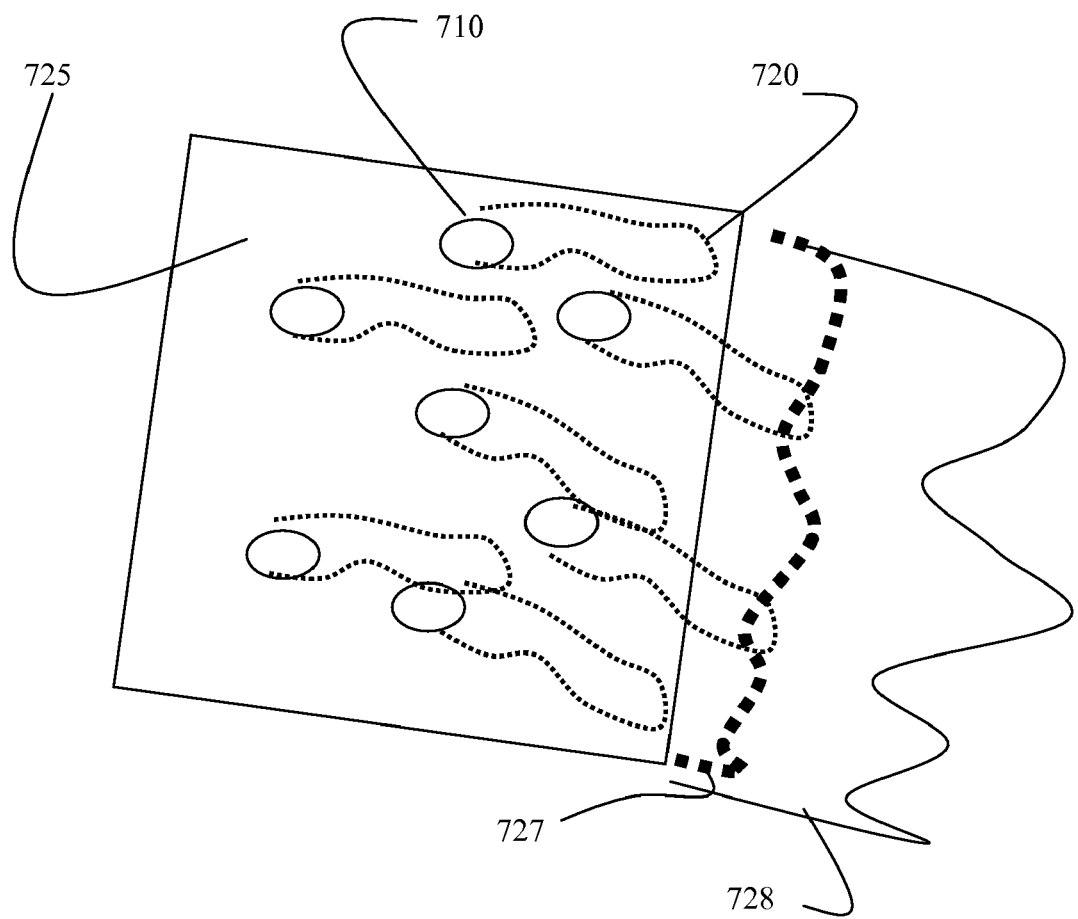
FIG. 7 is a simplified diagram showing a schematic representation of a surface of the skin or tissue treated with a pattern of thermal modification to minimize collateral damage and enhance healing time.

In FIG. 7, a pattern of treated spots 710 in the skin 725 is treated so that at least some tissue modification takes place and wherein the spaces between the spots are not treated. The extent of the spots stretch to a depth 720. The spot diameter of the treated zone is as described above. The percentage of the treated area can advantageously vary from 5% to 95%, more preferably from 20% to 80%, more preferably yet from 30% to 70% and most preferably from 40% to 60%. In especially preferred embodiments, the tissue can be modified in a region extending from the surface to a depth of between about 25 micrometers to about 750 micrometers and more preferably from about 50 micrometers to about 400 micrometers. The percentage of the modified or thermally modified tissue to unchanged tissue is preferably from about 0% to about 70% and more preferably between 3% and 50%. The dotted line 727 represents the epidermal dermal junction and the line 728 represents the boundaries of the dermis. The depth 720 within which the tissue is modified thus extends to either the epidermis, the dermis, or both.

Thus, specific embodiments and applications of skin treating apparatus and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device for treating a region of intact living skin having a surface and an epidermal/dermal junction, comprising:
   an energy source;
   a treatment head comprising an electrical resistance heater, a treatment tip having an area of between 0.2 cm2 and 9 cm2 configured to be placed against a skin surface, and a layer of electrically insulating but thermally conducting material in thermal contact with the treatment head, wherein the treatment head is configured to provide a thermal energy pulse at the treatment tip responsive to energy provided by the energy source; and
   a controller that cooperates with the energy source to provide sufficient energy to the electrical resistance heater to heat the treatment tip and thereby create the energy pulse with the treatment head, wherein the controller controls and limits the energy provided to the electrical resistance heater such that the energy is provided to the electrical resistance heater to create an energy pulse having a duration of no more than 100 sec, and the energy pulse delivers an average energy density of 5 J/cm$^2$ or less from the treatment tip, and heats the treatment tip to a temperature of at least 50 degrees Celsius.

2. The device of claim 1 wherein the energy pulse has an energy density of 0.7 J/cm$^2$ to 3 J/cm$^2$.

3. The device of claim 1 wherein the energy pulse has a duration of less than 1 sec.

4. The device of claim 1 wherein the controller cooperates with the energy source and treatment head to provide a second energy pulse, wherein the energy pulse and second energy pulse are both provided within a 20 second period.

5. The device of claim 1 wherein the controller cooperates with the energy source and treatment head to provide a second energy pulse with an interpulse delay of between 0.2 sec and 10 sec, inclusive, between the energy pulse and second energy pulse.

6. The device of claim 1 wherein the energy source and the controller are located in a common hand-holdable housing.

7. The device of claim 1 wherein a first side of the layer of thermally conducting material defines a treatment area.

8. The device of claim 1, wherein the electrical resistance heater comprises a conductor in a flat configuration to thereby provide a generally flat planar diffusion of heat from the treatment head.

9. The device of claim 1, wherein the treatment head further comprises a temperature monitor, and wherein the device is configured to prevent, after the energy pulse, delivery of further energy pulses from the energy source to the treatment head until after the temperature of the treatment head drops below a selected value.

10. A device comprising:
   a hand-holdable housing;
   an energy source, wherein the energy source comprises a battery and a capacitor;
   a heating element comprising a resistive heater and a treatment tip, wherein the treatment tip comprises a diameter of between 0.2 mm and 10 cm;
     wherein the capacitor is configured to have a discharge capacity sufficient to provide a thermal energy pulse from the treatment tip of between 0.5 J/cm$^2$ and 5 J/cm$^2$, and to heat the treatment tip to a temperature of at least 50 degrees Celsius; and
   a controller configured to trigger the capacitor to release its discharge capacity to the heating element.

11. The device of claim 10, further comprising:
   a user interface on the hand-holdable housing, wherein the user interface comprises:
     a charge button configured to effectuate charging of the capacitor when the charge button is activated by a user; and
     a fire button configured to cause, the controller, when activated by the user, to trigger the capacitor to release its discharge capacity to the heating element.

12. The device of claim 11, wherein the resistive heater comprises a flat conductor.

13. The device of claim 10, wherein the energy source is configured to provide sufficient electrical energy to the heating element to heat the treatment tip to a temperature of at least 70 degrees Celsius.

14. The device of claim 10, wherein the energy source is configured to provide electrical energy to the heating element so as to provide the thermal energy pulse for a duration of no more than 100 seconds.

15. The device of claim 10, wherein the energy source is configured to provide electrical energy to the heating element so as to provide the thermal energy pulse for a duration of no more than 10 seconds.

16. A device for treating a region of intact living skin having a surface and an epidermal/dermal junction, comprising:
   an energy source;
   a treatment head comprising a thermal heater, a treatment tip comprising a layer of thermally conducting material in thermal contact with the thermal heater and comprising a diameter between 0.2 mm and 10 cm configured to be placed against a skin surface, wherein the treatment head is configured to provide a thermal energy pulse at the treatment tip responsive to energy provided by the energy source; and
   a controller that cooperates with the energy source to provide sufficient energy to the thermal heater to heat the treatment tip and thereby create the energy pulse with the treatment head, wherein the controller controls and limits the energy provided by the energy source such that the energy is provided to the thermal heater to create an energy pulse having a duration of no more than 100 sec, and the energy pulse delivers an average energy density of 5 J/cm$^2$ or less from the treatment tip, and heats the treatment tip to a temperature of at least 50 degrees Celsius.

17. The device of claim 16, wherein said thermal heater is selected from the group consisting essentially of a light source, an RF Source, an Ultrasound source, an EM energy source, and an electric heater.

18. The device of claim 16, wherein said thermally conducting material comprises a material capable of transferring said energy pulse to the skin.

19. The device of claim 16, wherein said thermally conducting material comprises an electrically insulating material.

20. The device of claim 16, wherein said treatment head further comprises a suction source.

21. The device of claim 16, wherein said thermal heater is selected from the group consisting essentially of a light source, an RF Source, an Ultrasound source, an EM energy source, an electric heater; and said treatment head comprises a material capable of transferring said energy pulse to the skin.

* * * * *